United States Patent [19]

Ishida et al.

[11] 4,332,770

[45] Jun. 1, 1982

[54] APPARATUS FOR ANALYZING THE CARBON CONTENT OF METALS

[75] Inventors: Kozo Ishida; Akimichi Kira, both of Kyoto, Japan

[73] Assignee: Horiba, Ltd., Kyoto, Japan

[21] Appl. No.: 199,217

[22] Filed: Oct. 21, 1980

[30] Foreign Application Priority Data

Nov. 17, 1979 [JP] Japan .................. 54-149665

[51] Int. Cl.$^3$ .................................. G01N 31/12
[52] U.S. Cl. .................. 422/78; 23/230 PC; 356/418; 422/80
[58] Field of Search .............. 422/78, 80; 23/230 PC, 23/232 R; 356/229, 437, 418

[56] References Cited

U.S. PATENT DOCUMENTS

| | | | |
|---|---|---|---|
| 3,305,318 | 2/1967 | Bennet | 422/78 X |
| 3,765,842 | 10/1973 | Purt | 23/232 R |
| 3,784,359 | 1/1974 | Parth | 23/230 PC |
| 3,985,505 | 10/1976 | Bredeweg | 23/230 PC |

*Primary Examiner*—Ronald E. Serwin
*Attorney, Agent, or Firm*—Wenderoth, Lind & Ponack

[57] ABSTRACT

An apparatus for analyzing carbon in metals, in which a metallic sample is burned in a current of oxygen in a combustion furnace and the concentration of carbon contained in the metallic sample is calculated from the total concentration of carbon monoxide and carbon dioxide in the gas generated in the combustion furnace, the concentration determined by means of a non-dispersive infrared analyzer. The non-dispersive infrared analyzer is provided with a detector which exhibits almost the same sensitivity to both carbon monoxide and carbon dioxide.

2 Claims, 4 Drawing Figures

APPARATUS FOR ANALYZING THE CARBON CONTENT OF METALS

BACKGROUND OF THE INVENTION

1. Field of the Invention

The present invention relates to an apparatus for analyzing the carbon content of metals, in which the metal sample to be analyzed is burned in a current of oxygen in a combustion furnace or a resistance furnace; the concentration of carbon dioxide and the like, contained in the gas generated in the furnace, is determined by means of a non-dispersive infrared analyzer; the carbon content of said metal sample is then calculated by an integration technique.

2. Description of the Prior Art

When a metallic sample is burned, all of the carbon contained therein is converted to carbon dioxide ($CO_2$) or carbon monoxide (CO). Accordingly, the carbon content of the metallic sample may be determined by measuring the $CO_2$ and CO concentrations. U.S. Pat. Nos. 3,305,318 and 3,985,505, respectively issued to E. L. Bennett and R. L. Bredeweg teach systems for determining the carbon content of a metallic sample from the measurement of the CO and $CO_2$ concentrations. The disclosure contained in these two patents are incorporated by reference herein.

In the case of prior art analyzers, as a rule, not only carbon dioxide, but also carbon monoxide is generated at a ratio of several percent therebetween, based on the content of carbon dioxide when the metal sample is burned. Accordingly, in the conventional apparatus as shown in FIG. 1, gas generated in a combustion furnace 3' is passed through an oxidizer 7' to convert carbon monoxide to carbon dioxide and then the concentration of carbon dioxide is determined by means of a non-dispersive infrared analyzer 9' of carbon dioxide or, as shown in FIG. 2, the concentration of carbon dioxide and carbon monoxide generated in a combustion furnace 3' is respectively determined by means of a non-dispersive infrared analyzer 9'a of carbon dioxide and a non-dispersive infrared analyzer 9'b of carbon monoxide; the measurement values of analyzers 9a and 9b are then added electrically by means of an adder 10'. Referring now to FIG. 1 and FIG. 2, 1' designates an oxygen cylinder, 2' designating a refiner, 4' designating a dust filter, 5' designating a desiccating agent and 6' designating a flow rate regulator.

However, in the former prior art system (FIG. 1), the use of said oxidizer 7' leads to the oxidation of $SO_2$, contained in the gas generated in said combustion furnace 3', to $SO_3$ which interferes with the determination of carbon dioxide. Consequently it is necessary to use an $SO_3$-removing agent 8'.

In the latter prior art system (FIG. 2), two pairs of infrared analyzer 9'a and 9'b, and adder 10' are required, resulting in a plurality of expensive elements. Accordingly, the apparatus cost and the resulting analyzing costs become high.

SUMMARY OF THE INVENTION

It is an object of the present invention to provide an apparatus for analyzing the carbon content of metals, which is economical because it does not require an oxidizer, $SO_3$-removing agent and an adder, and because it requires only one infrared analyzer.

DESCRIPTION OF THE PREFERRED EMBODIMENT

The present invention will be more clearly understood by reference to FIG. 3 and FIG. 4 hereinafter.

Figure 1:
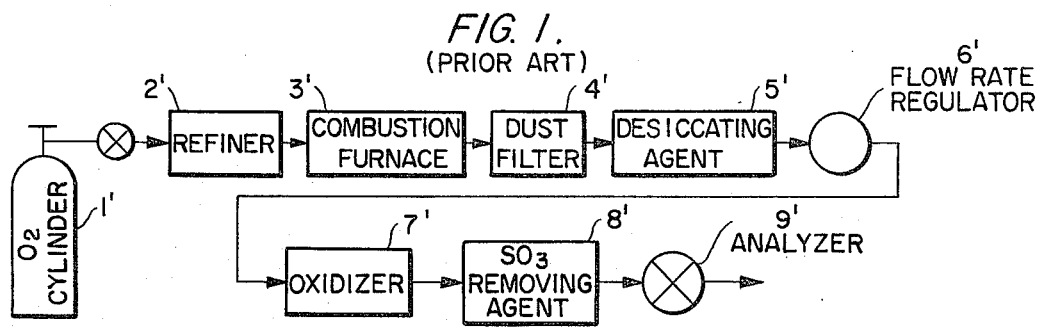
FIG. 1 and FIG. 2 are block diagrams of conventional prior art apparatus.
Figure 2:
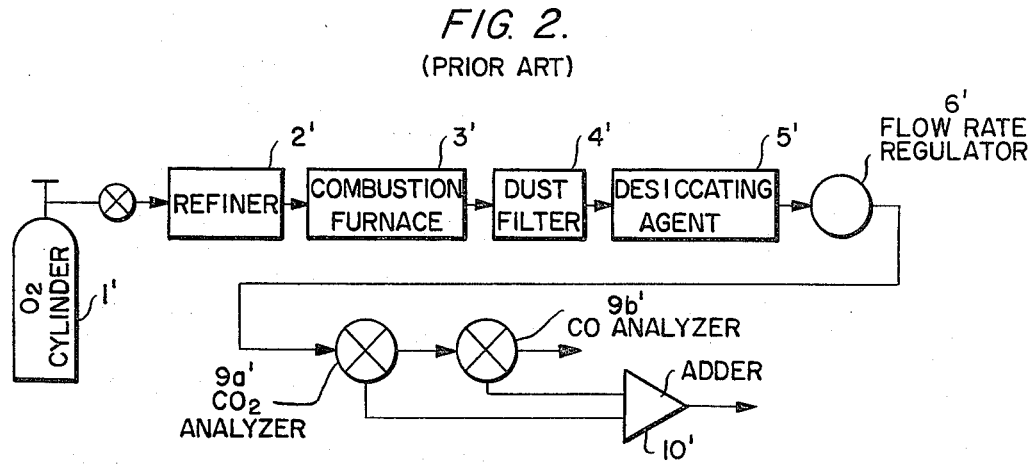
Figure 3:
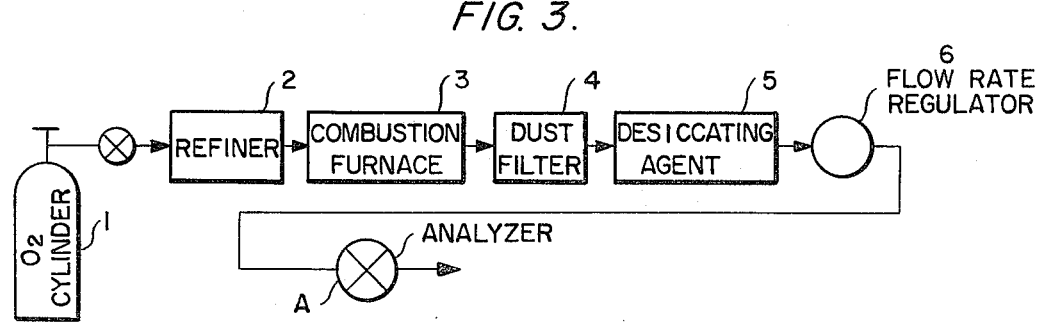
FIG. 3 is a block diagram showing an example of the apparatus for analyzing carbon in metals according to the present invention.

FIG. 3 is a block diagram showing an example of the apparatus for analyzing the carbon content of metals according to the present invention, in which 1 designates an oxygen cylinder, 2 designates a refiner for removing impurities contained in said oxygen cylinder, and 3 designates a combustion furnace, such as high-frequency furnace or a resistance furnace for burning metallic samples contained in a crucible in a current of oxygen. Gas generated in said combustion furnace 3 is passed through a dust filter 4, desiccating agent 5 and a flow rate regulator 6 for adjusting the flow rate of gas to a predetermined suitable value. A non-dispersive infrared analyzer A is provided with a detector which exhibits almost the same degree of sensitivity to both carbon monoxide and carbon dioxide and is connected to the output of said flow rate regulator.

Figure 4:
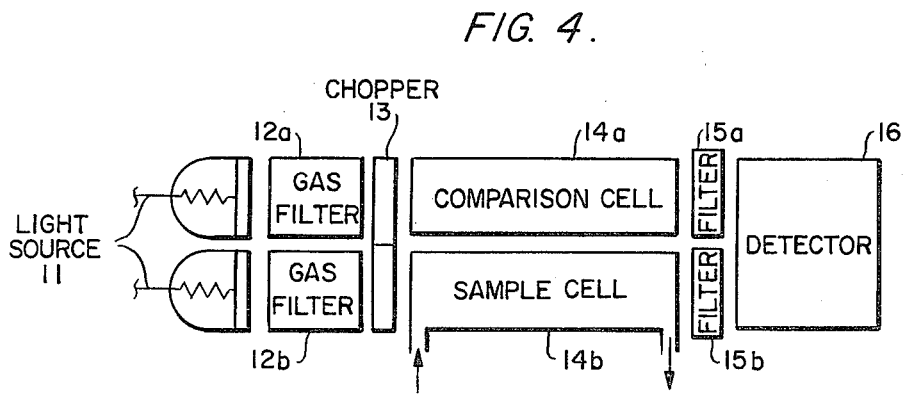
FIG. 4 is a schematic view showing the arrangement of the main parts of the example shown in FIG. 3.

FIG. 4 shows an example of said analyzer A, in which 11 designates a light source, 12a, 12b designates a gas filter, 13 designates a chopper, 14a designates a comparison cell, 14b designates a sample cell, 15a, 15b designates a solid filter which eliminates the interferences of all gases excepting carbon monoxide and carbon dioxide, and passes only the infrared rays which are absorbed by carbon monoxide and carbon dioxide, and 16 designates a detector having a sensitivity to both carbon monoxide and carbon dioxide, for example, a pyroelectric detector or a detector of the condenser microphone type containing a gaseous mixture consisting of carbon monoxide and carbon dioxide as the gas for absorbing infrared rays therein so that it may exhibit a sensitivity to both carbon monoxide and carbon dioxide. When a detector of the condenser microphone type is used, said solid filter 15a, 15b in not required. U.S. Pat. No. 4,180,733 to S. Ueda teaches the details of a conventional detector corresponding to detector 16.

Said gas filter 12a, 12b serves for adjusting the ratio of the sensitivity to carbon monoxide to the sensitivity to carbon dioxide of said detector 16 so as to be equal to 1:1. Carbon dioxide is contained in said gas filter 12a, 12b if the ratio of the sensitivity to carbon monoxide to the sensitivity to carbon dioxide of said detector 16 itself ($CO/CO_2$) is smaller than one ($CO/CO_2 < 1$), and carbon monoxide is contained in said gas filter 12a, 12b if said sensitivity ratio ($CO/CO_2$) is larger than one ($CO/CO_2 > 1$). Accordingly, said gas filter 12a, 12b is not required if said sensitivity ratio ($CO/CO_2$) is equal to one ($CO/CO_2 = 1$).

As the above analyzer A, a non-dispersive infrared analyzer of fluid modulation type as disclosed in the German Auslegeschrift 29 00 624 (now German Pat. No. 2,900,624) and U.S. Pat. Application Ser. No. 972,485 (now U.S. Pat. No. 4,256,964) can be used.

According to the above described arrangement, although carbon monoxide is also generated in small amounts in addition to the generation of carbon dioxide when said metallic sample is burned in a current of oxygen in said combustion furnace 3, the output of said analyzer A shows the total concentration of carbon monoxide and carbon dioxide because said detector 16 exhibits a sensitivity to both carbon dioxide and carbon monoxide and said sensitivity ratio ($CO/CO_2$) is adjusted by means of said gas filter 12a, 12b. The concentration of carbon contained in said metallic sample can be calculated by means of a calculator not shown in the figure.

Although it is possible to adjust the ratio of the sensitivity to carbon monoxide to the sensitivity to carbon dioxide to 1:1 without using said gas filter 12a, 12b by suitably selecting the mixture ratio of carbon monoxide to carbon dioxide in the gaseous mixture to be enclosed in said pneumatic detector, in practice it has been found preferable to adjust said sensitivity ratio ($CO/CO_2$) by means of said gas filter 12a, 12b under the condition that the gaseous mixture consisting of carbon monoxide and carbon dioxide contained in said pneumatic detector is set at a ratio such that the sensitivity of the pneumatic detector to both carbon monoxide and carbon dioxide is at its highest value.

According to the present invention, it is possible to provide a remarkably simple and economical apparatus for analyzing the carbon content of metals, in which the total concentration of carbon dioxide and carbon monoxide generated by burning the metallic sample can be determined by means of only one non-dispersive infrared analyzer and the content of carbon in said metallic sample can be calculated from said total concentration of carbon dioxide and carbon monoxide without using a $SO_3$-removing agent which is required if an adder and an oxidizer are employed.

What is claimed is:

1. An apparatus for analyzing the carbon content of a metallic sample by utilizing a furnace for burning the metallic sample to be analyzed in a current of oxygen so as to generate a gas and comprising a single non-dispersive infrared analyzer having a single detector means for detecting both carbon monoxide and carbon dioxide, said single detector means exhibiting substantially the same sensitivity to both carbon monoxide and carbon dioxide in said gas generated in said furnace.

2. An apparatus as in claim 1, wherein said analyzer comprises:
   first and second light sources;
   first and second gas filters respectively arranged adjacent said first and second light sources;
   a chopper means operatively arranged to intermittently interupt light rays emanating from said first and second light sources through said first and second gas filters;
   a comparison cell arranged adjacent said chopper means to receive light emanating from said first light source and passing through said first gas filter and said chopper means;
   a sample cell arranged adjacent said chopper means to receive light emanating from said second light source and passing through said second gas filter and said chopper means;
   first and second filter means respectively arranged adjacent said comparison cell and sample cell to selectively remove bands of infrared radiation;
   a detector means for detecting infrared rays corresponding to a particular band of infrared frequencies.

* * * * *